US011401318B2

(12) United States Patent
Le Maoult et al.

(10) Patent No.: US 11,401,318 B2
(45) Date of Patent: Aug. 2, 2022

(54) MULTIMERIC POLYPEPTIDES OF HLA-G INCLUDING AT LEAST TWO ALPHA3 DOMAINS AND PHARMACEUTICAL USES THEREOF

(71) Applicant: COMMISSARIAT A L'ENERGIE ATOMIQUE ET AUX ENERGIES ALTERNATIVES, Paris (FR)

(72) Inventors: Joel Le Maoult, Melun (FR); Edgardo Delfino Carosella, Paris (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 460 days.

(21) Appl. No.: 15/868,119

(22) Filed: Jan. 11, 2018

(65) Prior Publication Data

US 2018/0194830 A1    Jul. 12, 2018

Related U.S. Application Data

(62) Division of application No. 13/379,525, filed as application No. PCT/IB2010/052917 on Jun. 25, 2010, now abandoned.

(30) Foreign Application Priority Data

Jun. 25, 2009   (WO) .................. PCT/IB2009/006491

(51) Int. Cl.
*A61K 39/00* (2006.01)
*C07K 14/74* (2006.01)

(52) U.S. Cl.
CPC ...... *C07K 14/70539* (2013.01); *A61K 39/001* (2013.01)

(58) Field of Classification Search
None
See application file for complete search history.

(56) References Cited

U.S. PATENT DOCUMENTS

2004/0210037 A1   10/2004   Zauderer

FOREIGN PATENT DOCUMENTS

| WO | 2007 011044 | 1/2007 |
| WO | 2010 052228 | 5/2010 |
| WO | 2010 150235 | 12/2010 |

OTHER PUBLICATIONS

LeMaoult et al (FASEB J, 2013, 27: 3643-3651) (Year: 2013).*
Megret et al (Human Immunol. 2007, 68(4): 294-302) (Year: 2007).*
Rosado et al (2008, Human Immunol. 69: 9-15) (Year: 2008).*
Baumgart and Sandborn (Lancet, 2012, 380: 1590-1605) (Year: 2012).*
Zalante et al (Inflam. Bowel Dis. 2011 17: E94-E95) (Year: 2011).*
Clements, C.S., et al., "Structural Studies on HLA-G: Implications for Ligand and Receptor Binding," Human Immunology, vol. 68, No. 4, pp. 220-226, (Apr. 4, 2007).
Li, C., et al., "HLA-G homodimer-induced cytokine secretion through HLA-G receptors on human decidual macrophages and natural killer cells," Proceedings of the National Academy of Sciences of the United States of America, vol. 106, No. 14, pp. 5767-5772. (Apr. 2009).
International Search Report dated Mar. 10, 2011 in PCT/IB10/52917 Filed Jun. 25, 2010.
WebMD (May 2015, pp. 1-5).
Athersys (2015, 4 pages).
Carosella et al (Blood 2008, 111(10): 4862-4870).
Witman et al (Molec. Immunol. 2000, 37:141-149).
Doniz-Padilla et al (Eur. J. Endocrinol. 2011, 165: 129-136.
LeMaoult et al (FASEB Journal, published online Jun. 10, 2013, 27:1-9.
Robinson and Sauer (PNAS 1998, 95(11): 5929-5934.
Carosella et al (Trends in Immunology, 2008, 29 (3): 125-132.
Fayen et al (Mol. Immunol. 1995, 2(4): 267-275.

* cited by examiner

*Primary Examiner* — G. R. Ewoldt
*Assistant Examiner* — Marianne DiBrino
(74) *Attorney, Agent, or Firm* — Oblon, McClelland, Maier & Neustadt, L.L.P.

(57) ABSTRACT

Multimeric polypeptides and pharmaceutical uses thereof; multimers of alpha3 peptides of an HLA-G antigen and methods of producing such multimers, pharmaceutical compositions comprising the same, as well as their uses for treating various diseases including organ/tissue rejection. The multimers include at least two monomers, each of said monomers being selected in the group consisting of a peptide P1 of formula X1-X2, wherein X1 represents a peptidic linker including a cysteine amino acid and X2 represents an alpha3 domain of HLA-G.

11 Claims, 8 Drawing Sheets

Figure 1:
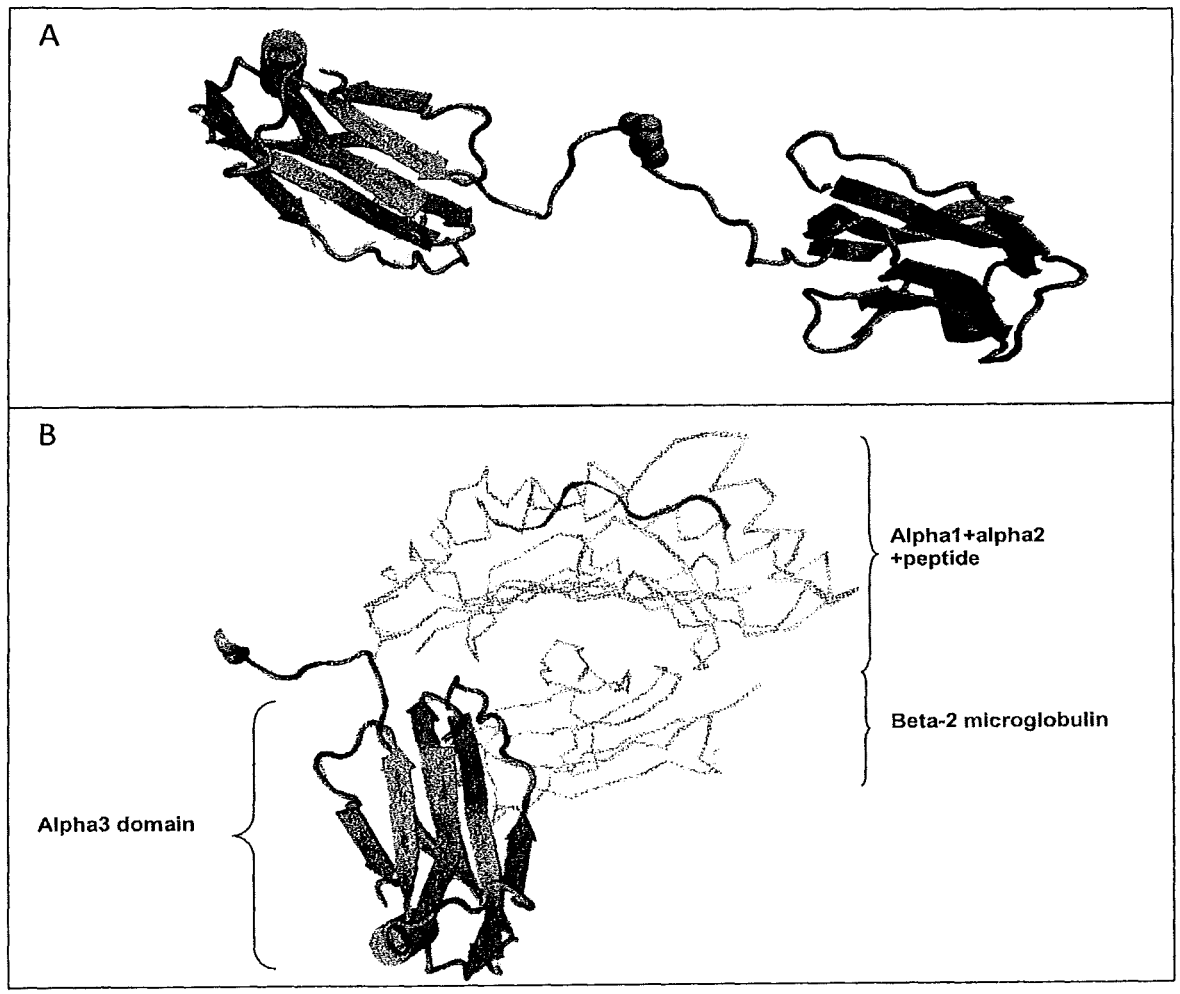

Specification includes a Sequence Listing.

(alpha3_L1) Peptide

GCGGGSGGGGSRADPPKTHVTHHPVFDYEATLRCWALGFYPAEIILTWQ
RDGEDQTQDVELVETRPAGDGTFQKWAAVVVPSGEEQRYTCHVQHEGLP
EPLMLRWKQ (SEQ ID NO:3)

(alpha3_L2) Peptide

CASDSDFRVFQTDKEMLQRADPPKTHVTHHPVFDYEATLRCWALGFYPAEII
LTWQRDGEDQTQDVELVETRPAGDGTFQKWAAVVVPSGEEQRYTCHVQH
EGLPEPLMLRWKQ (SEQ ID NO:5)

Alpha1-Alpha3 (HLA-G6) Peptide alpha1  GSHSMRYFSAAVSRPGRGEPRFIAMGYVDDTQFVRFDSDSACPRME
        PRAPWVEQEGPEYWEEETRNTKAHAQTDRMNLQTLRGYYNQSEADP alpha3  PKTHVTHHPVFDYEATLRCWALGFYPAEIILTWQRDGEDQTQDVELV
        ETRPAGDGTFQKWAAVVVPSGEEQRYTCHVQHEGLPEPLMLRWKQ (SEQ ID NO:4)

MULTIMERIC POLYPEPTIDES OF HLA-G INCLUDING AT LEAST TWO ALPHA3 DOMAINS AND PHARMACEUTICAL USES THEREOF

This application is a divisional of U.S. application Ser. No. 13/379,525 filed Mar. 20, 2012, pending and incorporated herein by reference, which is a National Stage Application of PCT/IB2010/052917 filed Jun. 25, 2010.

The present invention relates to multimeric polypeptides and pharmaceutical uses thereof. The invention more specifically relates to multimers comprising alpha 3 domains of an HLA-G antigen. The invention also relates to methods of producing such multimers, pharmaceutical compositions comprising the same, as well as their uses for treating various diseases including organ/tissue rejection.

Major histocompatibility complex (MHC) antigens are divided up into three main classes, namely class I antigens, class II antigens (HLA-DP, HLA-DQ and HLA-DR), and class III antigens.

Class I antigens comprise classical antigens, HLA-A, HLA-B and HLA-C, which exhibit 3 globular domains ($\alpha 1$, $\alpha 2$ and $\alpha 3$) associated with beta2 microglobulin, as well as non classical antigens HLA-E, HLA-F, and HLA-G.

HLA-G is a non-classic HLA Class I molecule expressed by extra-villous trophoblasts of normal human placenta, thymic epithelial cells and cornea. HLA-G antigens are essentially expressed by the cytotrophoblastic cells of the placenta and function as immunomodulatory agents protecting the foetus from the maternal immune system (absence of rejection by the mother). The sequence of the HLA-G gene has been described [1,2] and comprises 4396 base pairs. This gene is composed of 8 exons, 7 introns and a 3' untranslated end, corresponding respectively to the following domains: exon 1: signal sequence, exon 2: alpha1 extracellular domain, exon 3: alpha2, extracellular domain, exon 4: alpha 3 extracellular domain, exon 5: transmembrane region, exon 6: cytoplasmic domain I, exon 7: cytoplasmic domain II (untranslated), exon 8: cytoplasmic domain III (untranslated) and 3' untranslated region.

Seven isoforms of HLA-G (SEQ ID NO:6) have been identified, among which 4 are membrane bound (HLA-G1, HLA-G2, HLA-G3 and HLA-G4) and 3 are soluble (HLA-G5, HLA-G6 and HLA-G7) (see [3] for review).

The mature HLA-G1 protein isoform comprises the three external domains ($\alpha 1$, $\alpha 2$ and $\alpha 3$), the transmembrane region and the cytoplasmic domain.

The HLA-G2 protein isoform does not comprise the $\alpha 2$ domain, i.e., the $\alpha 1$ and $\alpha 3$ domains are directly linked, followed by the transmembrane domain and the cytoplasmic domain.

The HLA-G3 protein isoform lacks both the $\alpha 2$ and $\alpha 3$ domains, i.e., it comprises the $\alpha 1$ domain directly linked to the transmembrane domain and the cytoplasmic domain.

The HLA-G4 protein isoform lacks the $\alpha 3$ domain, i.e., it comprises the $\alpha 1$ domain, the $\alpha 2$ domain, the transmembrane domain and the cytoplasmic domain.

Soluble HLA-G isoforms all lack the transmembrane and cytoplasmic domains. More specifically:

The HLA-G5 protein isoform contains the $\alpha 1$, $\alpha 2$ and $\alpha 3$ domains, as well as an extra C-terminal peptide sequence of 21 amino acid residues encoded by intron 4 (as a result of intron 4 retention after transcript splicing and RNA maturation).

The HLA-G6 protein isoform corresponds to the HLA-G5 without $\alpha 2$, i.e., HLA-G6 contains $\alpha 1$ and $\alpha 3$ domains, as well as an extra C-terminal peptide sequence of 21 amino acid residues encoded by intron 4 (as a result of intron 4 retention after transcript splicing and RNA maturation).

The HLA-G7 protein isoform contains only the alpha1 domain, as well as 2 additional C-terminal amino acid residues encoded by intron2 (as a result of intron 2 retention after transcript splicing and RNA maturation).

All of these isoforms have been described in [4,5,6] and European Application EP 0 677 582.

Previous studies have shown that HLA-G proteins are able to inhibit allogeneic responses such as proliferative T lymphocyte cell response, cytotoxic T lymphocytes mediated cytolysis, and NK cells mediated cytolysis [7,8,9]. More recent studies have also shown that HLA-G is capable of inducing the differentiation of regulatory T cells, which can then inhibit allogeneic responses themselves, and are known to participate in the tolerance of allografts [10,11]. Because of this broad inhibitory function, it has been shown that the expression of HLA-G correlates with a better acceptance of allogeneic transplants, whether HLA-G is expressed by the graft or is detected in the plasma of patients, as a soluble molecule [12,13,14]. As a result, HLA-G-based procedures have been proposed for treating graft rejection in allogeneic or xenogenic organ/tissue transplantation. HLA-G proteins have also been proposed for the treatment of cancers (EP 1 054 688), inflammatory disorders (EP 1 189 627) and, more generally, immune related diseases. It has also been proposed to fuse HLA-G proteins to specific ligands in order to target HLA-G to particular cells or tissues (WO 2007/091078). It should be noted, however, that no results or experimental data have been provided to show that such targeting fusions are active.

HLA-G has been shown to bind three main receptors: ILT2/LILRB1/CD85j, ILT4/LILRB2/CD85d and KIR2DL4. ILT2 is mainly expressed by T cells, B cells, NK cells, monocytes, and dendritic cells. ILT4 is expressed only by myeloid cells, i.e. mainly monocytes and dendritic cells. KIR2DL4 is mainly expressed by decidual NK cells and by a small subset of peripheral NK cells. Due to the broad expression patterns of its inhibitory receptors, HLA-G may exert its tolerogenic function on all the effectors of immune responses that are responsible for anti-viral immunity, auto-immune reactions, anti-tumor immunity, inflammatory diseases, and rejection of transplants.

KIR2DL4 is a specific receptor for HLA-G. KIR2DL4 docks on the alpha1 domain of HLA-G, and more specifically on residues Met$^{76}$ and Gln$^{79}$ which are characteristic to HLA-G [15]. It was further shown that these two residues are crucial to the inhibitory function of HLA-G through KIR2DL4, and that mutating them prevented the inhibition of cytolytic activity of KIR2DL4-expressing NK cells by HLA-G in vitro. In spite of its specificity for HLA-G, KIR2DL4 is not likely to play a significant role in HLA-G inhibitory function except in the context of pregnancy, mainly because of its expression that is restricted to decidual NK cells, and because in vitro and in vivo, it was shown that ILTs played the key role through interaction with HLA-G alpha 3 domain. It is possible that the alpha1 domain of HLA-G plays a direct role in the function of HLA-G, through KIR2DL4 or another, as yet unknown receptor, but the evidence available to date points to a tolerogenic function of HLA-G that is mediated mainly if not entirely by the interaction of its alpha 3 domain with ILT2 and ILT4 molecules.

ILT2 and ILT4 are not specific receptors for HLA-G, and it was shown they can bind other HLA Class I molecules through their alpha 3 domain [16,17,18]. The capability of the HLA-Class I domain to bind to ILT molecules is well described. ILT2, in particular, has been reported to bind "most if not all" HLA Class I molecules.

However, HLA-G is the ligand of highest affinity for ILT2 and ILT4, as illustrated in Table 1 of Shiroishi et al [19].

Thus ILT2 and ILT4 bind more strongly to HLA-G than to classical HLA class I molecules. (see [20,21]).

This stronger ILT-binding capacity of HLA-G compared to other HLA Class I molecules is particularly well illustrated by the fact that HLA-G at the surface of tumor cells, but not classical HLA class I molecules are capable to engage the ILT2 and/or ILT4 receptors of cytolytic effectors with sufficient strength to block the function of these effectors and thus protect the tumor cells from immune destruction [22].

ILT2 and ILT4 do not bind the same HLA-G structures [21]. Indeed, ILT2 recognizes only β2 microglobulin (β2m)-associated HLA-G structures, whereas ILT4 has the capability to recognize both β2m-associated and β2m-free HLA-G heavy chains [21,23]. Yet, ILT4 clearly binds β2m-free HLA-G heavy chains better that β2m-associated ones.

HLA-G antigen appears to adopt a dimer conformation in vivo as a result of the formation of an intermolecular disulfide bridge between cysteine residue 42 of the α1 domains of two HLA-G molecules [20,23 and 25; WO2007/011044].

The dimeric structure of HLA-G has been described in Shiroishi et al. [20]. Two molecules of wild-type HLA-G exist in an asymmetric unit; each monomer is covalently attached with the symmetrical partner via the Cys42-Cys42 disulfide bridge along with 2-fold crystallographic axis. The full-length HLA-G1 protein is composed of H chain, associated β2-microglobulin (β2m) and a nonameric peptide similar to the classical MHC class I structure. It has been proposed that receptor binding sites of HLA-G dimers are more accessible than those of corresponding monomers, so that dimers would have a higher affinity and slower dissociation rate than monomers. However, it is not clear what conformation is the most active for pharmaceutical purpose, which isoform is the most efficient, or how appropriate HLA-G dimers or oligomers may be produced.

It emerges from the foregoing that the superior inhibitory function of HLA-G is due:

1. To a unique sequence of its alpha 3 domain which confers it a better ILT-binding capacity than that of other HLA Class I molecules. This unique sequence of the HLA-G alpha 3 domain, as it emerges from FIG. 3 of Shiroishi et al., [21] leads to the creation of larger, more hydrophobic, and stronger ILT-binding area.

Figure 4:
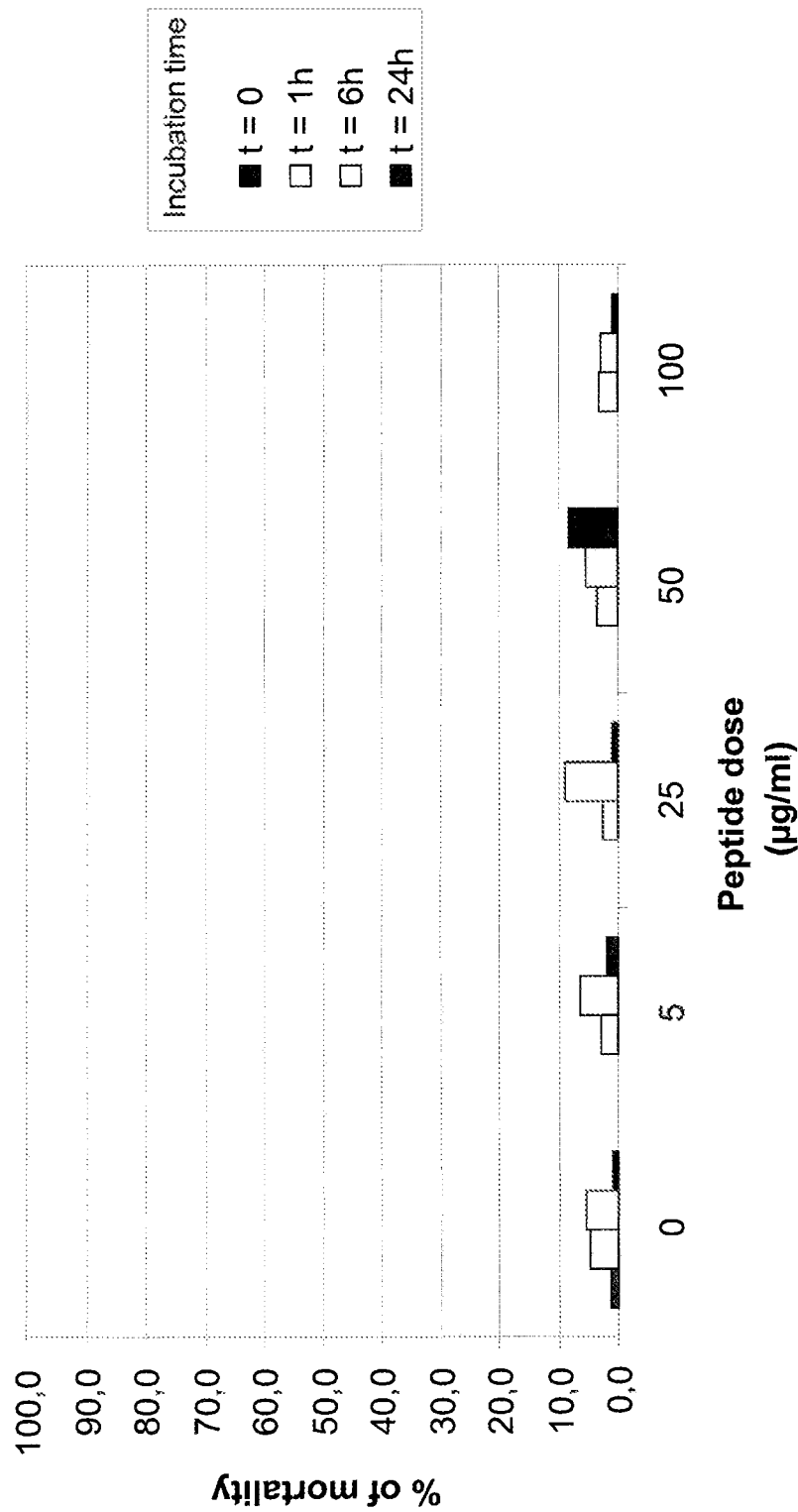

2. To its unique ability to dimerize. Dimerization of HLA-G occurs via the creation of disulfide bridges between the cysteines in position 42 (alpha 1 domain) of two HLA-G molecules (see FIG. 8 of Gonen-Gross et al. [24]) and is crucial to HLA-G function. Indeed, it was shown that mutant HLA-G molecules that lack the cysteine in position 42 and do not make dimers also lack inhibitory function [24]. FIG. 4 of Shiroishi et al [20] provides the disulfide linked HLA-G dimer structure.

Thus, to summarize the data on HLA-G inhibitory function: it goes mainly through the binding of HLA-G dimers to ILT molecules through their unique alpha 3 domain. However, the ILT4/HLA-G complex structure [21] reveals that ILT4 shows remarkably distinct major histocompatibility class I (MHCI) binding recognition compared to ILT2, binding more to the α3 domain than to β2m.

Producing HLA-G through cell lines may be tedious. Indeed, the complete HLA-G1/G5 molecule is a trimolecular complex of a HLA-G complete heavy chain (α1, α2 and α3 domains) non-covalently associated with β2m and a nonapeptide. The function of such a construct is well established, but due to the complexity of its structure, its production is difficult, its purification risky, and its stability is poor.

The Inventors have now found that unexpectedly, multimers of small peptides containing only alpha 3 domain of HLA-G (SEQ ID NO:1), which may be obtained synthetically, are functional, more pure, therefore more stable, easier to produce because they do not require neither extraction from biological fluids, nor specific control (because said production does not involve biological agents), thus decreasing the risk of biohazard, following GMP practices: because GMP practices have safety standards in terms of biohazard which are lifted here.

Thus, the present invention relates to multimers or multimeric polypeptides, characterized in that they comprise at least two monomers, each of said monomers being selected in the group consisting of a peptide P1 (named also here after alpha 3 monomer) of formula X1-X2, wherein X1 represents a flexible peptidic linker including a cysteine amino acid and X2 represents an alpha 3 domain (SEQ ID NO:1) (or alpha 3 peptide) of HLA-G.

Thus the multimers of the invention include dimers of formula P1-P1 and multimers of formula (P1)n, comprising exclusively alpha 3 monomers (SEQ ID NO:3 or SEQ ID NO:5).

The following multimers are also included in the instant invention:

homomultimers of alpha 3 monomers (n P1 monomers), wherein all the monomers are identical;

heteromultimer of alpha 3 monomers (n P1 monomers, wherein the α3 domain of different monomers is different), n being an integer comprised between 2 and 1000 or even more.

The multimers according to the invention thus include dimers, as well as molecules comprising 3, 4, 5, 6, 7 or even more P1 monomers. Multimers according to the instant invention may comprise up to 100, 500, 1000 or even more P1 monomers.

The inventors have shown that unexpectedly, multimers comprising at least two alpha 3 monomers (SEQ ID NO:3 or SEQ ID NO:5) (also named alpha 3 polypeptides) effectively inhibit graft rejection in vivo. More specifically, the inventors have surprisingly found that alpha 3 monomers, when correctly assembled in multimers, have the ability to induce efficient immune tolerance in vivo, more specifically in graft rejection.

HLA-G antigens function as immunomodulatory agents protecting the foetus from the maternal immune system. Various HLA-G isoforms have been reported, which are either membrane-bound or soluble. These isoforms contain distinct functional domains, selected from extracellular globular domains, designated α1 (SEQ ID NO:2), α2 and α3 (SEQ ID NO:1), a trans-membrane domain and a cytoplasmic domain. While the biological activity and mechanism of action of certain HLA-G isoforms (such as mature HLA-G1) have been documented, the relative contribution of each domain to the immunoregulatory activity, especially in soluble form, has not been studied in detail.

In this regard, as specified above, it has been documented that the inhibitory activity of HLA-G antigen is mediated by binding to ILT inhibitory receptors ILT2 or ILT4. More specifically, it has been proposed that such binding occurs through the alpha 3 domain of HLA-G (Shiroishi et al., [21]).

The inventors have now observed that alpha 3 polypeptides, comprising only alpha 3 domains of HLA-G (SEQ ID NO:1) are able to protect graft rejection in vivo or inhibition of alloproliferation in vitro.

The results obtained show that the multimers according to the instant invention exhibit high immunoregulatory activity in vivo and therefore represent efficient drugs for treating immune-related disorders, particularly for reducing unwanted or deleterious immune responses in a subject. The results obtained more specifically show that multimers of this invention can induce a 100% or even more increase in graft survival in vivo compared to placebo or α1-α3 multimers comprising at least two monomers, each of said monomers consisting of a peptide comprising from the N-terminal end to the C-terminal end an alpha1 domain of HLA-G and an alpha 3 domain of HLA-G (named indifferently hereafter alpha 3-alpha1 monomer or alpha1-alpha 3 monomer although the alpha1 domain is always at the N-terminal end).

Indeed, the alpha 3 multimers of the invention are significantly more efficient compared to soluble HLA-G6 isoform, alpha 3 multimers comprising a non flexible peptidic linker or alpha1-alpha 3 multimers.

These multimers thus represent very valuable drug candidates for treating such disorders, as well as other immune-related diseases, such as inflammatory diseases or auto-immune, such as psoriasis or atopic dermatitis.

According to the instant invention:
- peptide P1 may also at the C-terminal end and/or at the N-terminal end of X2 comprise less than 20, more preferably less that 15 and most preferably less than 10 or 5 additional amino acids which flank the alpha 3 domain in a native HLA-G isoform.
- The flexible peptidic linker X1 comprises at least 10-30 amino acids and includes a cysteine at its N-terminal end, preferably in positions 1, 2, 3 or 4 from the N-terminal end (see SEQ ID NO:3, for instance, wherein linker L1, corresponding to aminoacids 1-12 (SEQ ID NO:7), presents in position 2 from its N-terminal end a cysteine); it may be longer to gain more flexibility (up to 100 amino acids). Said flexible peptidic linker essentially comprises glycine, serine and threonine amino acid residues; more preferably it essentially comprises glycine and serine amino acid residues.
- X2 comprising an alpha 3 domain (SEQ ID NO:1) or peptide designates a peptide comprising the amino acid sequence of an alpha 3 domain of an HLA-G antigen, or a functional fragment thereof, and essentially devoid of other HLA-G domains. More preferably, the alpha 3 peptide comprises the amino acid sequence of an alpha 3 domain of a HLA-G antigen (SEQ ID NO:1). In a multimer of the invention, it is preferred that all alpha 3 monomers have the same amino acid sequence. However, it is also contemplated that alpha 3 peptides of different sequence are present in a multimer of the invention.
- The alpha 3 domain (SEQ ID NO:1) of HLA-G is encoded by exon 4 and corresponds to amino acids 207-298 of the human HLA-G of SEQ ID NO:6.
- The alpha1 domain (SEQ ID NO:2) of HLA-G is encoded by exon 2, and corresponds to amino acids 25-114 of the human HLA-G of SEQ ID NO:6.
- A "functional fragment" designates a fragment which retains the ability to induce graft tolerance in vivo and/or inhibition of alloproliferation in vitro. More preferably, a functional fragment of alpha 3 peptides comprises at least 20, more preferably at least 30, 40 or 50 consecutive amino acids of the alpha 3 domain.

In a typical embodiment, the functional fragment contains at least 60 consecutive amino acids of the alpha 3 domain. The functionality of the fragment may be verified as disclosed in the experimental section. In particular, the functionality may be verified by preparing a multimer of the fragments, administering the multimer to an animal model prior to organ/tissue transplantation, and verifying the graft survival rate. Where the multimer extends the duration of graft survival by 50%, as compared to placebo, the fragment may be considered as functional.

- The amino acid sequence of the α1 and α3 domains can be derived directly from the publications of Geraghty et al. [1], or Ellis et al. [2]. These sequences are also available on line (see for instance Genebank numbers for HLA-G: first cloning of genomic sequence: Geraghty et al, PNAS 1987: PubMed ID: 3480534, GeneID: 3135; First cloning of HLA-G1 cDNA: Ellis et al Journal of Immunology 1990. PubMed ID: 2295808).

Furthermore, the sequences of HLA-G5, HLA-G6 and HLA-G7 are also available from U.S. Pat. Nos. 5,856,442, 6,291,659, FR2,810,047, or Paul et al., Hum. Immunol 2000; 61: 1138, from which the sequence of the alpha1 and alpha 3 domain can be obtained directly.

- It should be understood that natural variants of HLA-G antigens exist, e.g., as a result of polymorphism, which are included in the present application. Also, variants of the above sequences which contain certain (e.g., between 1 and 10, preferably from 1 to 5, most preferably 1, 2, 3, 4 or 5) amino acid substitutions or insertions are also included in the present invention.
- the term "multimer" (or multimeric polypeptide) designates a molecule (or a composition or product) comprising at least two P1 monomers (P1-P1) as defined above (i.e. alpha 3 monomers associated together through a disulfide bridge) or a carrier.

In a specific embodiment, the alpha 3 peptide consists essentially of amino acids 183-274 of a mature HLA-G antigen, or a functional fragment thereof.

The alpha 1 peptide consists essentially of amino acids 1-90 of a mature HLA-G antigen, or a functional fragment thereof.

The sequence of a preferred alpha 3 peptide is provided in SEQ ID NO:1.

The sequence of alpha1 peptide is provided in SEQ ID NO:2.

The sequence of a preferred alpha 3 monomer is provided in SEQ ID NO:3 (alpha 3–L1). The linker L1 corresponds to positions 1-12 (SEQ ID NO:7) and contains a cysteine in position 2; positions 13 and 14 correspond to two amino acids of the alpha2 domain (see SEQ ID NO:6 corresponding to HLA-G and in which alpha2 corresponds to positions 115-206). Positions 15-106 correspond to the alpha 3 domain and positions 107-108 correspond to two amino acids of the transmembrane domain; all the hydrophilic tail of HLA G may be inserted. Main contact residues with ILT molecules are in positions 27 and 29 of said SEQ ID NO:3.

Another sequence of an alpha 3 monomer is provided in SEQ ID NO:5. The linker L2 corresponds to positions 1-18 (SEQ ID NO:8) and contains a cysteine in position 1; positions 19 and 20 correspond to two amino acids of the alpha2 domain (see SEQ ID NO:6 corresponding to HLA-G and in which alpha2 corresponds to positions 115-206).

Positions 21-111 correspond to the alpha 3 domain and positions 112-113 correspond to two amino acids of the transmembrane domain.

The sequence of alpha1-alpha 3 monomer is provided in SEQ ID NO:4. Positions 1-90 of SEQ ID NO:4 correspond to alpha1 domain; positions 91-182 of SEQ ID NO:4 correspond to alpha 3 domain and positions 183-184 correspond to two amino acids of the transmembrane domain; all the hydrophilic tail of HLA G may be inserted. Cys42 is used for dimerization. Main contact residues with ILT molecules are in positions 103 and 105.

Within multimers of the instant invention, the various monomers may be linked together in different manner such as, without limitation, through disulfide bridging (especially for a dimer), or through a spacer group and/or a carrier.

In a preferred embodiment of the instant invention, the alpha 3 monomers, as defined here above are linked covalently or through an affinity interaction.

A particular example of a multimer of the invention is a P1-P1 dimer.

In this respect, the invention relates to an alpha 3 dimer, having two monomers P1 of SEQ ID NO:3 associated together through a disulfide bridge. More specifically, the two alpha 3 peptides are linked through a disulfide bridge between cysteine residues present at the N terminus of the linker X1.

In a further particular embodiment, the alpha 3 monomers are linked through a spacer or a carrier. In a particular embodiment, monomers are linked to a carrier, thereby producing a multimer. The carrier can be of different nature. It is preferably biocompatible, and most preferably biologically inert. The carrier may be a molecule, such as a protein, e.g., albumin (e.g., human serum albumin), or an inert solid carrier. The monomers may be linked to the carrier through different types of coupling reactions, such as affinity interaction or the use of functional groups. Affinity interaction may be obtained by coating the carrier with ligands that bind alpha 3 or alpha1 peptides (e.g., antibodies or fragments thereof). Affinity interaction may also be obtained by adding to the alpha 3 monomers and to the carrier, respectively a member of a binding pair (e.g., avidin and biotin). Coupling may also be obtained through bi-functional groups such as maleimide, etc. Furthermore, it should be noted that multimers may contain monomers linked to a carrier and further engaged in intermolecular disulfide bridging.

In a particular embodiment, a multimer of the instant invention is a molecule comprising two or more alpha 3 monomers (SEQ ID NO:3 or SEQ ID NO:5) linked to a carrier.

The multimers of this invention can be produced by various techniques. As discussed above, the monomers may be coupled together through different coupling techniques, such as covalent linkage (e.g., disulfide bridge, bi-functional group, etc) or affinity reaction.

For the production of a multimer of alpha 3 monomers P1 (SEQ ID NO:3 or SEQ ID NO:5) as defined above through disulfide linkage:
- in a first step, two alpha 3 monomers P1 (SEQ ID NO:3 or SEQ ID NO:5) comprising a lateral SH group (provided by peptidic linker X1 (SEQ ID NO:7 or SEQ ID NO:8)) are contacted in solution, under conditions allowing formation of a disulfide linkage; in a second step and, preferably, the dimers or multimers are separated. Multimers may be separated from monomers, e.g., on the basis of their molecular weight, e.g., by gel electrophoresis (such as PAGE). The suitable formation of multimers may also be verified using such method on aliquot samples, to measure the relative amount of multimer present in the solution and, if necessary, adjust the reaction condition. Conditions allowing formation of disulfide linkage include, for instance, a temperature of 10-30° C. for 2-24 hours.

Alpha1-alpha 3 multimers may be obtained in the same conditions, from alpha1-alpha 3 monomers obtained by chemical synthesis.

For the production of a multimer through the use of a carrier, the monomers are typically incubated in the presence of the carrier under conditions allowing attachment of the monomers on the carrier and, preferably, the multimer is separated. The carrier may be e.g., a solid carrier. The carrier may also be a protein, such as serum-albumin. In order to facilitate interaction between the monomers and the carrier, the carrier may be functionalized to contain reactive groups able to interact with the monomers. As an example, the carrier may be coated with a ligand of alpha1 or alpha 3 peptides (SEQ ID NO:1 and SEQ ID NO:2), such as antibodies or fragments thereof (e.g., Fab fragments, CDR fragments, ScFv, etc) or a chemical coupling reagent (e.g., maleimide). Alternatively, the carrier may be functionalized by a reactant able to bind a ligand of the alpha1 polypeptides. As an example, the carrier may be coated with an anti-human IgG Fc fragment, and the ligand may be a human polyclonal IgG directed against an HLA-G1 antigen. In such a case, the monomers, carrier and ligand may be incubated together, in order to allow proper association of the monomers to the beads.

Alpha 3 multimers of the invention may be produced by techniques known per se in the art, such as recombinant techniques, enzymatic techniques or artificial synthesis, preferably by artificial synthesis, such as the Merrifield synthesis.

In a preferred embodiment, the alpha 3 peptides X2 (SEQ ID NO:1) and the alpha 3 monomers P1 (SEQ ID NO:3 or SEQ ID NO:5) are produced by artificial synthesis using known chemistry and synthesisers.

The alpha 3 multimers may comprise either natural amino acids, or non-natural or modified amino acid residues. They may be in L and/or D conformation. The peptides may comprise either amine linkages and/or modified peptidomimetic linkages. Also, the peptides may be terminally protected and/or modified, e.g., through chemical or physical alteration of lateral functions, for instance.

In further embodiment, the carrier and monomers may be modified to contain cross-reactive groups (e.g., avidin and biotin). In such a case, incubation of the carrier and monomers will cause multimerisation on the carrier.

The multimer formed (i.e., the complex between the carrier and the alpha 3 monomer) can be isolated using various techniques known per se in the art, including centrifugation, sedimentation, electromagnetic separation, etc.

Specific examples of multimers of the invention are:
- multimers of alpha 3 monomers of SEQ ID NO:3 linked through disulfide bridge;
- multimers of alpha 3 monomers of SEQ ID NO:3 linked to a carrier such as a microbead.

As mentioned in the examples, these multimers are able to promote graft tolerance in vivo.

Furthermore, the dimers of alpha 3 monomer of SEQ ID NO:3 also represent specific objects of the invention. The invention indeed shows that said dimers have substantial in vivo activity for treating graft rejection and may be used to prepare very active multimers.

The invention also relates to a pharmaceutical composition comprising a multimer as defined above or obtainable by a method as disclosed above and, preferably, at least a pharmaceutically acceptable vehicle or carrier.

A further object of this invention is a pharmaceutical composition comprising an alpha 3 dimer having two monomers of SEQ ID NO:3 and, preferably, at least a pharmaceutically acceptable vehicle or carrier.

Suitable vehicles or carriers include any pharmaceutically acceptable vehicle such as buffering agents, stabilizing agents, diluents, salts, preservatives, emulsifying agents, sweeteners, etc. The vehicle typically comprises an isotonic aqueous or non aqueous solution, which may be prepared according to known techniques. Suitable solutions include buffered solutes, such as phosphate buffered solution, chloride solutions, Ringer's solution, and the like. The pharmaceutical preparation is typically in the form of an injectable composition, preferably a liquid injectable composition, although other forms may be contemplated as well, such as tablets, capsules, syrups, etc. The compositions according to the invention may be administered by a number of different routes, such as by systemic, parenteral, oral, rectal, nasal or vaginal route. They are preferably administered by injection, such as intravenous, intraarterial, intramuscular, intraperitoneal, or subcutaneous injection. Transdermal administration is also contemplated. The specific dosage can be adjusted by the skilled artisan, depending on the pathological condition, the subject, the duration of treatment, the presence of other active ingredients, etc. Typically, the compositions comprise unit doses of between 10 ng and 100 mg of multimer, more preferably between 1 µg and 50 mg, even more preferably between 100 µg and 50 mg. The compositions of the present invention are preferably administered in effective amounts, i.e., in amounts which are, over time, sufficient to at least reduce or prevent disease progression. In this regard, the compositions of this invention are preferably used in amounts which allow the reduction of a deleterious or unwanted immune response in a subject.

Said multimeric polypeptides can be used as tolerogenic agents capable of mimicking HLA-G full function. The prime therapeutic uses of these compounds would be transplantation, in order to induce and maintain tolerance to allografts, but may also be auto-immune diseases, or inflammatory diseases, in order to stop auto-immune responses and inflammation, and possibly re-establish auto-tolerance. The advantages of such polypeptides are production/purification protocols comparatively easier, cheaper, more controlled, safer than classical production methods that involve prokaryotic or eukaryotic organisms and significantly more active than HLA-G6 isoform or control peptides as defined in the examples [(alpha 3–L2)×2 of SEQ ID NO:5 and (alpha1-alpha 3)×2] of SEQ ID NO:4.

As mentioned above, the multimers (SEQ ID NO:3 or SEQ ID NO:5) of the instant invention have strong immune-regulatory activity and may be used to treat a variety of disease conditions associated with abnormal or unwanted immune response. More specifically, the multimers of the invention are suitable for treating immune-related disorders such as, particularly, organ or tissue rejection, inflammatory diseases or auto-immune diseases. They can substantially inhibit allogeneic graft rejection in vivo.

The instant invention also relates to a multimer or composition as disclosed above for treating graft rejection.

The invention further relates to a method of treating graft rejection in a subject, the method comprising administering to a subject in need thereof an effective amount of a composition as disclosed above.

The term treating designates for instance the promotion of the graft tolerance within the receiving subject. The treatment can be performed prior to, during and/or after the graft, and may be used as an alternative therapy to existing immunosuppressive agents or, as a combined therapy with actual immunosuppressive agents. The invention is applicable to allogenic, semi-allogenic or even xenogenic transplantation, and may be used for any type of transplanted organs or tissues including, without limitation, solid tissues, liquid tissues or cells, including heart, skin, kidney, liver, lung, liver-kidney, etc.

The invention relates also to an improved method for transplanting an organ or tissue in a subject, the improvement comprising administering to the subject, prior to, during and/or after transplantation, an effective amount of a composition as disclosed above.

The invention further relates to a method for promoting graft tolerance in a subject, the method comprising administering to the subject, prior to, during and/or after transplantation, an effective amount of a composition as disclosed above.

The invention further relates to a method for reducing graft rejection in a subject, the method comprising administering to the subject, prior to, during and/or after transplantation, an effective amount of a composition as disclosed above.

In a preferred embodiment, the composition is administered at least twice to the subject. Indeed, the results shown in this application demonstrate that a repeated administration leads to a further increased benefit, e.g., to a further significantly increased graft tolerance in vivo.

It should be understood that the amount of the composition actually administered shall be determined and adapted by a physician, in the light of the relevant circumstances including the condition or conditions to be treated, the exact composition administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

Besides the above provisions, the invention also comprises other provisions that will emerge from the following description, which refers to examples of implementation of the present invention and also to the attached drawings, in which:

FIG. 1: 3D model of the (alpha 3)×2 dimer of SEQ ID NO:1. A Model of the dimerized polypeptide. Each monomer is in a different grey. The artificially introduced free cysteine is shown by spheres, allowing dimerization. B: Superimposition of the structure of the alpha 3 peptide with that of the complete HLA-G molecule. HLA-G complete molecule (including beta-2 microglobulin and peptide) is shown in light threads. Alpha 3 peptide is shown in 3D ribbon rendering. The structures of the alpha 3 domain of HLA-G and of the alpha 3 peptide are superimposed.

Figure 2:
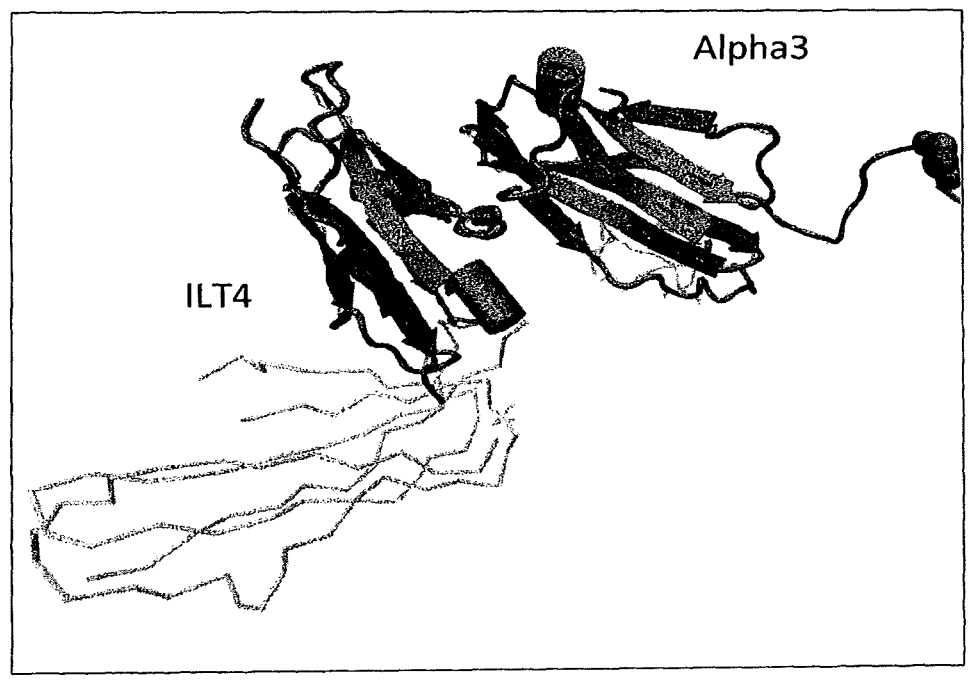

FIG. 2: 3D model of the binding of the (Alpha 3)×2 of SEQ ID NO:1 polypeptide to ILT4 molecules. Only one half of the (alpha 3)×2 dimer is shown.

Figure 3:
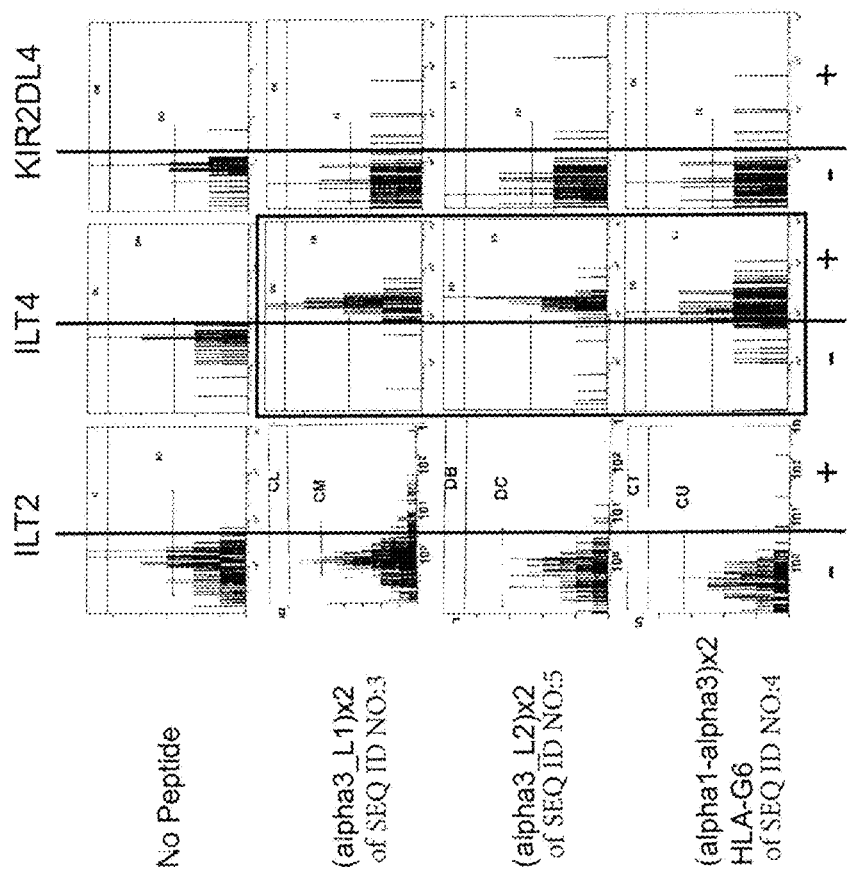

FIG. 3: Binding of different dimers to HLA-G receptors ILT2, ILT4, KIR2DL4: (alpha 3–L1)×2 of SEQ ID NO:3; P1-P1 dimer according to the invention) wherein L1 (SEQ ID NO:7) represents a particular linker X1; (alpha 3–L2)×2 of SEQ ID NO:5: control peptide; (alpha 3–alpha1)×2 of SEQ ID NO:4: control peptide. A peak that is situated on the right of the vertical bar indicates recognition by the indicated receptor.

FIG. 4: Cell toxicity results.

Figure 5:
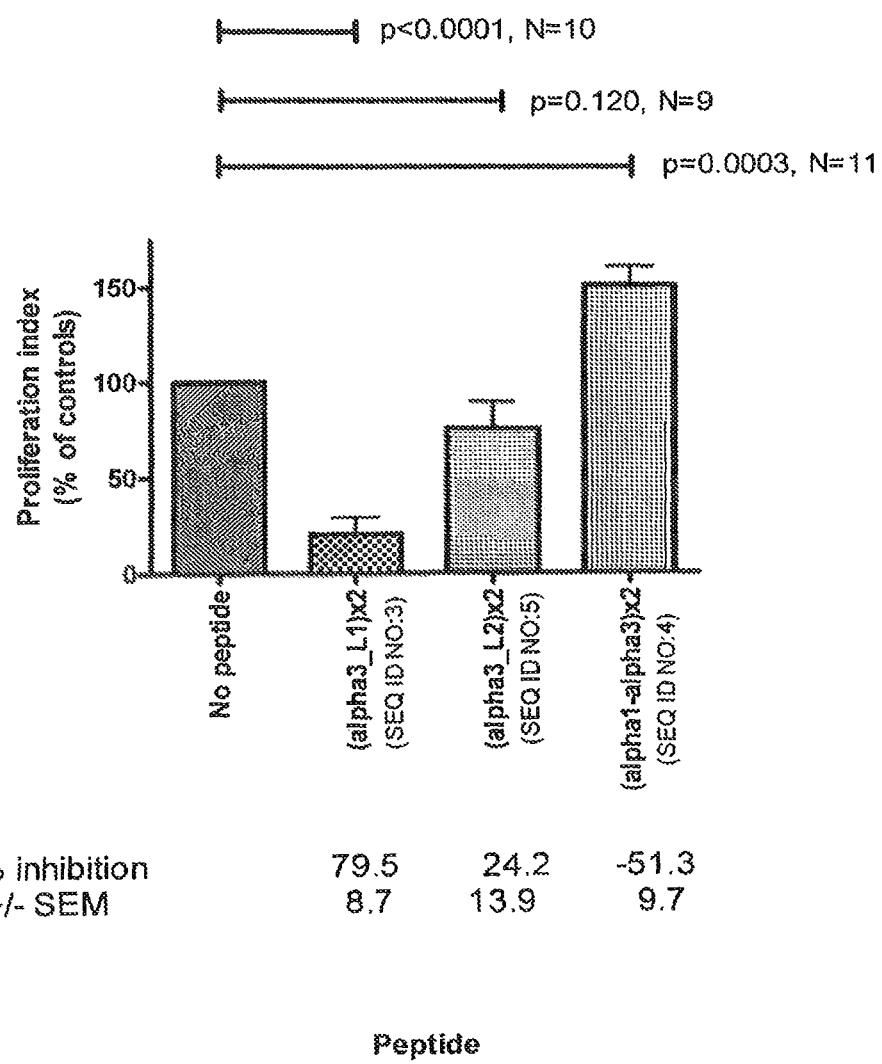

FIG. 5: Effect of different peptides on the alloproliferation of T lymphocytes in vitro: (alpha 3–L1)×2 of SEQ ID NO:3: P1-P1 dimer according to the invention) wherein L1 represents a particular linker X1 (SEQ ID NO:7); (alpha 3–L2)×2 of SEQ ID NO:5: control peptide; (alpha1–alpha 3)×2 of SEQ ID NO:4: control peptide. Bar graph: proliferation indexed on controls, SEM are reported as error bars. % inhibition: represents the extent of inhibition mediated by the peptides.

Figure 6:
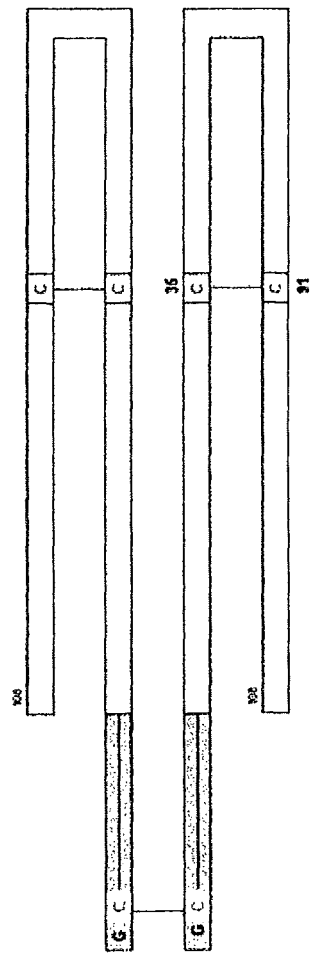

FIG. 6: General structures of (alpha 3–L1)×2 of SEQ ID NO:3 and (alpha 3–L2)×2 of SEQ ID NO:5 dimers.

Figure 7:
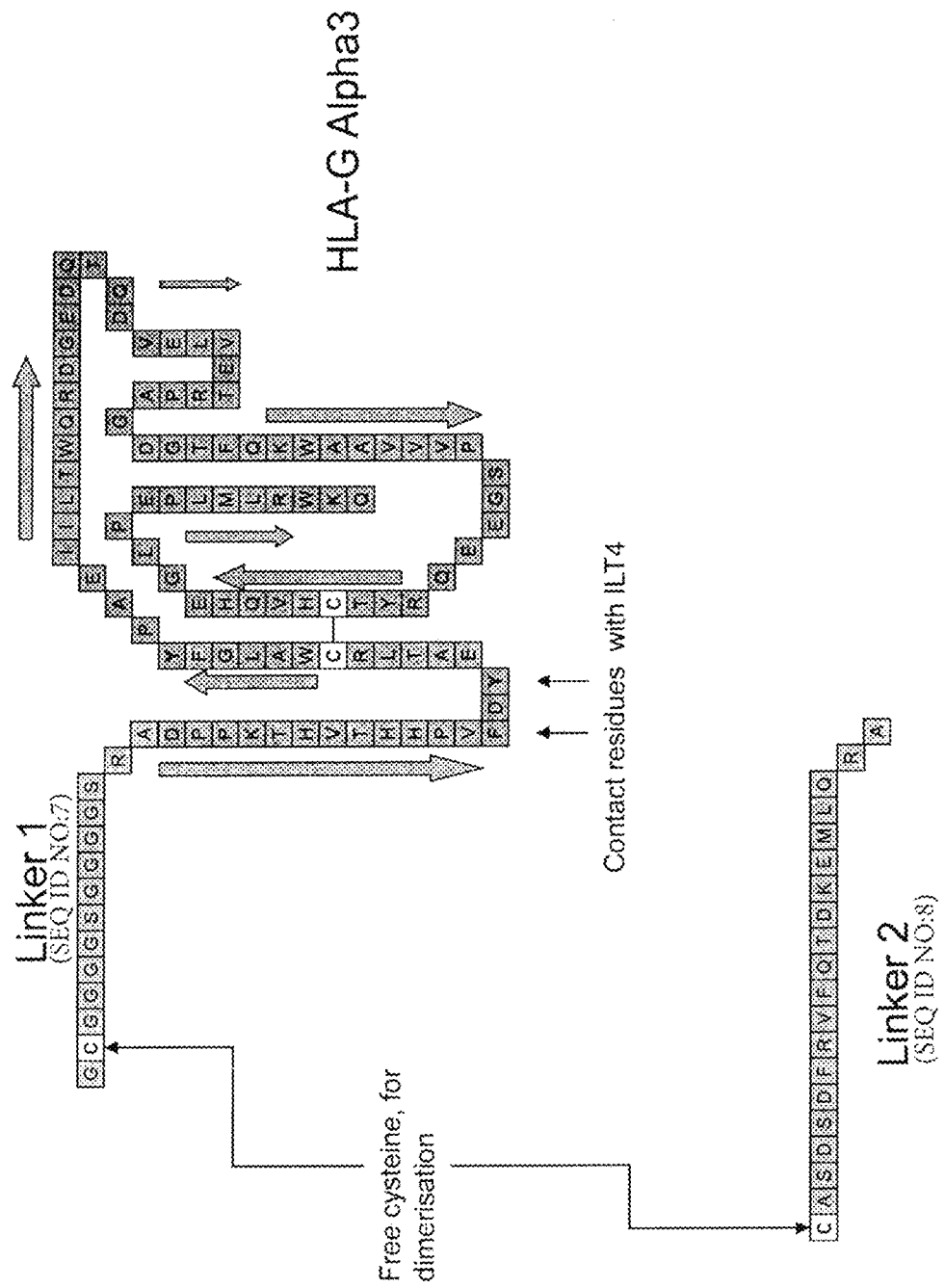

FIG. 7: Structural scheme of alpha 3-L1 of SEQ ID NO:3 and alpha 3-L2 of SEQ ID NO:5 monomers. The HLA-G Alpha3 sequence is SEQ ID NO:1.

Figure 8:
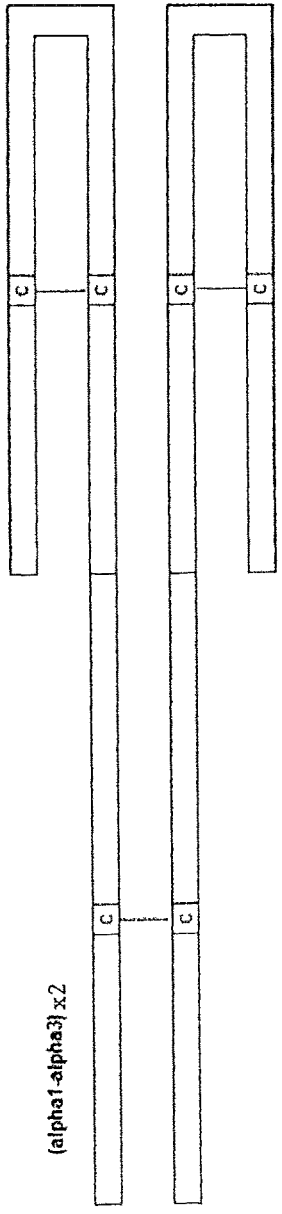

FIG. 8: General structure of (alpha 3–alpha1)×2 dimers.

EXAMPLE 1: PREPARATION OF PEPTIDES OF SEQ ID NO:1-5

The peptides of SEQ ID NO:1-5 were synthesised using a peptide synthesiser.

Different dimers have been produced:
(alpha 3–L1)×2 (SEQ ID NO:3), wherein L1 (SEQ ID NO:7) corresponds to a flexible peptidic linker according to the invention, i.e. comprising mainly glycine and serine amino acid residues;
(alpha 3–L2)×2 (SEQ ID NO:5), wherein L2 (SEQ ID NO:8) corresponds to amino acids 1-18 of said SEQ ID NO:5 and is derived from alpha1 amino acid residues 42-30 (from N-terminal and to C-terminal end) of HLA-G (see SEQ ID NO:6);
(alpha1–alpha 3)×2; SEQ ID NO:4 corresponds to an alpha1–alpha 3 monomer.

FIGS. 6, 7 and 8 illustrate the general structures of the synthesized peptides.

EXAMPLE 2: ALPHA 3 AND ALPHA 3-ALPHA1 DIMERS THROUGH DISULFIDE LINKAGE

1) Alpha 3 Dimers of SEQ ID NO:3 or SEQ ID NO:5

Alpha 3 monomers of SEQ ID NO:3 or SEQ ID NO:5 were synthesized chemically. Monomers were first synthesized, then refolded by allowing the generation of disulfide bonds between the two cysteines within the alpha 3 domain (cysteines 35 and 91 of SEQ ID NO:3, cysteines 41 and 97 of SEQ ID NO:5). Dimerization was then performed by generating a disulfide bridge between the cysteines within the linker X1 of two monomers (Cysteine 2 of SEQ ID NO:3, cysteine 1 of SEQ ID NO:5). The purity of the synthesized products was verified by mass spectrometry.

Visualization of alpha 3 multimers was achieved by eletrophoresis separation: samples were denatured by heat in presence of Laemmli buffer in non-reducing condition (without β-mercaptoethanol), and then separated by electrophoretic migration in a 12% SDS-PAGE. The presence of dimers was then visualized after coloration by coomassie blue.

A three dimensional model of the dimer of SEQ ID NO:3 is shown in FIG. 1. Based on computational modelization, this structure is able to bind HLA-G receptor ILT4 (shown in FIG. 2; see also FIG. 3).

2) Alpha1-Alpha 3 Dimers of SEQ ID NO:4

Alpha1–alpha 3 monomers of SEQ ID NO:4 were synthesized chemically. Monomers were first synthesized, then refolded by allowing the generation of disulfide bonds between the two cysteines within the alpha 3 domain (cysteines 111 and 167 of SEQ ID NO:4). Dimerization was then performed by generating a disulfide bridge between two cysteines within the alpha1 domain of two monomers (Cysteine 42 of SEQ ID NO:4). The purity of the synthesized products was verified by mass spectrometry.

Visualization of alpha 3 multimers was achieved by eletrophoresis separation: samples were denatured by heat in presence of Laemmli buffer in non-reducing condition (without β-mercaptoethanol), and then separated by electrophoretic migration in a 12% SDS-PAGE. The presence of dimers was then visualized after coloration by coomassie blue.

The sequence of the alpha1+alpha 3 polypeptide is shown in SEQ ID NO:4.

EXAMPLE 3: RECEPTOR BINDING ASSAYS

To test the binding to HLA-G receptors ILT2, ILT4, and KIR2DL4, 12 μg of dimers obtained according to example 2 were covalently coated on Bio-Plex-COOH polystyrene beads (Bio-Rad) according to the manufacturer's recommendations. Beads were then resuspended at a concentration of 2000 beads per 50 μl in 1× Luminex assay buffer (Interchim). Recombinant receptors fused to the Fc part of a human IgG (ILT2-Fc, ILT4-Fc, R&D Biosystems) were then added at 2 μg/ml. Beads and receptors were then incubated for 90 minutes in the dark on a shaker before wash twice with 200 μl of 1×PBS, 0.05% Tween. Beads were then resuspended in 50 μl of PBS Luminex assay Buffer containing 2 μl g/ml of Phycoerythrin-conjugated Goat anti Human IgG antibody (Sigma) for 30 minutes in the dark on a rotating shaker. Beads were then washed twice with 200 μl of 1×PBS, 0.05% Tween, and resuspended in 300 μl of 1×PBS.

Fluorescence, indicative of peptide recognition by the receptors was evaluated by flow cytometry performed on an Epics XL Cytometer (Beckman Coulter) using EXPO32 software (Beckman Coulter).

FIG. 3 illustrates the results and clearly show that all peptides containing alpha 3 domain indeed bind specifically to ILT4 receptor.

EXAMPLE 4: CELL TOXICITY

Cell toxicity of the synthetic (alpha 3–L1)×2 dimer of SEQ ID NO:3 of example 1 was evaluated on freshly isolated peritheral mononuclear cells (PBMC) at 100,000 cells/ml in 200 μl wells, for doses of dimers ranging from 0 to 100 μg/ml and for incubation times ranging from 0 to 24 hours at 37° C. Toxicity was evaluated by analyzing cell viability using trypan blue incorporation in dead cells and calculation of the living cell vs dead cell ratio.

Results (FIG. 4) show that said dimers are not toxic towards PBMC.

EXAMPLE 5: MIXED LYMPHOCYTES REACTION (MLR)

Peripheral blood mononuclear cells (PBMC) from heparinized whole blood of healthy volunteer donors were obtained by density-gradient centrifugation over Ficoll-histopaque 1077 (Sigma-Aldrich). PBMC were used as responder or γ-irradiated stimulator cells (25 Gy). To evaluate the functions of synthetic peptides in allo-stimulation assays, $10^5$ responder cells in 10 μl were pre-incubated with peptide at a concentration of 100 μg/ml for 6 hours, and then mixed with $10^5$ γ-irradiated allogeneic stimulator PBMCs (25Gy) in 100 µl to obtain a final peptide concentration of 50 µg/ml in a final volume of 200 µl per well. All samples were run in triplicate, and for each allogeneic combination, responder cells alone, irradiated stimulated cells alone, autologous controls, and untreated controls were included. After a 5-day incubation at 37° C. and 5% $CO_2$ in a humidified incubator, the cultures were pulsed with tritiated thymidine (1 µCi per well, Amersham Biosciences). $^3$H thymidine incorporation into DNA was quantified 18 hours later on a β-counter (Wallac 1450, Amersham Biosciences).

FIG. 5 illustrates the results and shows that alpha 3 dimers according to the invention [(alpha 3–L1)×2 of SEQ ID NO:3 in said FIG. 5] inhibit significantly alloproliferation of T lymphocytes compared to (alpha 3–L2)×2 dimer of SEQ ID NO:5 and (alpha1–alpha 3)×2 dimer of SEQ ID NO:4.

REFERENCES

1. Geraghty D E, Koller B H, Orr H T (1987) A human major histocompatibility complex class I gene that encodes a protein with shortened cytoplasmic segment. Proc Natl Acad Sci USA 84: 9145-9149.
2. Ellis S A, Palmer M S, McMichael A J (1990) Human trophoblast and the choriocarcinoma cell line BeWo express a truncated HLA Class I molecule. J Immunol 144: 731-735.
3. Carosella, E. D., Dausset, J., Kirszenbaum, M. (1996) HLA-G revisited. Immunol Today 17: 407-409.
4. Kirszenbaum M, Moreau P, Gluckman E, Dausset J, Carosella E (1994) An alternatively spliced form of HLA-G mRNA in human trophoblasts and evidence for the presence of HLA-G transcript in adult lymphocytes. Proc Natl Acad Sci USA 91: 4209-4213.
5. Kirszenbaum M, Moreau P, Teyssier M, Lafon C, Gluckman E, et al. (1995) Evidence for the presence of the alternatively spliced HLA-G mRNA forms in human mononuclear cells from peripheral blood and umbilical cord blood. Hum Immunol 43: 237-241.
6. Moreau P, Carosella E, Teyssier M, Prost S, Gluckman E, et al. (1995) Soluble HLA-G molecule. An alternatively spliced HLA-G mRNA form candidate to encode it in peripheral blood mononuclear cells and human trophoblasts. Hum Immunol 43: 231-236.
7. Rouas-Freiss N, Marchal R E, Kirszenbaum M, Dausset J, Carosella E D (1997) The alpha1 domain of HLA-G1 and HLA-G2 inhibits cyto-toxicity induced by natural killer cells: is HLA-G the public ligand for natural killer cell inhibitory receptors? Proc Natl Acad Sci USA 94: 5249-5254.
8. Rouas-Freiss N, Goncalves R M, Menier C, Dausset J, Carosella E D (1997) Direct evidence to support the role of HLA-G in protecting the fetus from maternal uterine natural killer cytolysis. Proc Natl Acad Sci USA 94: 11520-11525.
9. Rouas-Freiss N, Khalil-Daher I, Riteau B, Menier C, Paul P, et al. (1999) The immunotolerance role of HLA-G. Semin Cancer Biol 9: 3-12.
10. LeMaoult J, Krawice-Radanne I, Dausset J, Carosella E D (2004) HLA-G1-expressing antigen-presenting cells induce immunosuppressive CD4+ T cells. Proc Natl Acad Sci USA 101: 7064-7069.
11. Naji A, Le Rond S, Durrbach A, Krawice-Radanne I, Creput C, et al. (2007) CD3+CD4low and CD3+CD8low are induced by HLA-G: novel human peripheral blood suppressor T-cell subsets involved in transplant acceptance. Blood 110: 3936-3948.
12. Lila N, Carpentier A, Amrein C, Khalil-Daher I, Dausset J, et al. (2000) Implication of HLA-G molecule in heart-graft acceptance. Lancet 355: 2138.
13. Creput C, Durrbach A, Menier C, Guettier C, Samuel D, et al. (2003) Human leukocyte antigen-G (HLA-G) expression in biliary epithelial cells is associated with allograft acceptance in liver-kidney transplantation. J Hepatol 39: 587-594.
14. Qiu J, Terasaki P I, Miller J, Mizutani K, Cai J, et al. (2006) Soluble HLA-G Expression and Renal Graft Acceptance. Am J Transplant 6: 2152-2156.
15. Yan W H, Fan L A (2005) Residues met76 and gln79 in HLA-G alpha1 domain involve in KIR2DL4 recognition. Cell Res 15: 176-182.
16. Colonna M, Navarro F, Bellon T, Llano M, Garcia P, et al. (1997) A common inhibitory receptor for major histocompatibility complex class I molecules on human lymphoid and myelomonocytic cells. J Exp Med 186: 1809-1818.
17. Colonna M, Samaridis J, Cella M, Angman L, Allen R L, et al. (1998) Human myelomonocytic cells express an inhibitory receptor for classical and nonclassical MHC class I molecules. J Immunol 160: 3096-3100.
18. Allan D S, Colonna M, Lanier L L, Churakova T D, Abrams J S, et al. (1999) Tetrameric complexes of human histocompatibility leukocyte antigen (HLA)-G bind to peripheral blood myelomonocytic cells. J Exp Med 189: 1149-1156.
19. Shiroishi M, Tsumoto K, Amano K, Shirakihara Y, Colonna M, et al. (2003) Human inhibitory receptors Ig-like transcript 2 (ILT2) and ILT4 compete with CD8 for MHC class I binding and bind preferentially to HLA-G. Proc Natl Acad Sci USA 100: 8856-8861.
20. Shiroishi M, Kuroki K, Ose T, Rasubala L, Shiratori I, et al. (2006) Efficient Leukocyte Ig-like Receptor Signaling and Crystal Structure of Disulfide-linked HLA-G Dimer. J Biol Chem 281: 10439-10447.
21. Shiroishi M, Kuroki K, Rasubala L, Tsumoto K, Kumagai I, et al. (2006) Structural basis for recognition of the nonclassical MHC molecule HLA-G by the leukocyte Ig-like receptor B2 (LILRB2/LIR2/ILT4/CD85d). PNAS 103: 16412-16417.
22. Caumartin J, Favier B, Daouya M, Guillard C, Moreau P, et al. (2007) Trogocytosis-based generation of suppressive NK cells. EMBO J 26: 1423-1433.
23. Gonen-Gross T, Achdout H, Arnon T I, Gazit R, Stern N, et al. (2005) The CD85J/Leukocyte Inhibitory Receptor-1 Distinguishes between Conformed and {beta}2-Microglobulin-Free HLA-G Molecules. J Immunol 175: 4866-4874.
24. Gonen-Gross T, Achdout H, Gazit R, Hanna J, Mizrahi S, et al. (2003) Complexes of HLA-G protein on the cell surface are important for leukocyte Ig-like receptor-1 function. J Immunol 171: 1343-1351.
25. Boyson J E, Erskine R, Whitman M C, Chiu M, Lau J M, et al. (2002) Disulfide bond-mediated dimerization of HLA-G on the cell surface. Proc Natl Acad Sci USA 99: 16180-16185.
26. Riteau B, Moreau P, Menier C, Khalil-Daher I, Khosrotehrani K, et al. (2001) Characterization of HLA-G1, -G2, -G3, and -G4 isoforms transfected in a human melanoma cell line. Transplant Proc 33: 2360-2364.
27. Lila N, Amrein C, Guillemain R, Chevalier P, Latremouille C, et al. (2002) Human leukocyte antigen-G expression after heart transplantation is associated with a reduced incidence of rejection. Circulation 105: 1949-1954.

The invention claimed is:

1. A method for treating graft rejection or promoting graft tolerance in a subject in need thereof, comprising administering to said subject an effective amount of a multimer comprising two monomers, each independently a peptide P1 of formula X1-X2, wherein X1 is SEQ ID NO:7, and X2 has the sequence SEQ ID NO: 1, and wherein the two monomers are linked through a disulfide bridge between cysteine residues on the flexible peptidic linker X1, or administering a pharmaceutical composition comprising the multimer.

2. The method of claim 1, wherein the peptide P1 comprises less than 20 additional amino acids at the C-terminal end of X2, less than 20 additional amino acids at the N-terminal end of X2, or less than 20 additional amino acids at each of the C-terminal end and the N-terminal end of X2, wherein the additional amino acids flank the alpha 3 domain in a native HLA-G isoform.

3. The method of claim 1, wherein the peptide P1 comprises less than 15 additional amino acids at the C-terminal end of X2, less than 15 additional amino acids at the N-terminal end of X2, or less than 15 additional amino acids at each of the C-terminal end and the N-terminal end of X2, wherein the additional amino acids flank the alpha 3 domain in a native HLA-G isoform.

4. The method of claim 1, wherein the peptide P1 comprises less than 10 additional amino acids at the C-terminal end of X2, less than 10 additional amino acids at the N-terminal end of X2, or less than 10 amino acids at each at of the C-terminal end and the N-terminal end of X2, wherein the less than 10 additional amino acids flank the alpha 3 domain in a native HLA-G isoform.

5. The method of claim 1 wherein the peptide PI comprises less than 5 additional amino acids at the C-terminal end, less than 5 additional amino acids at the N-terminal end, or less than 5 additional amino acids at each of the C-terminal end and the N-terminal end of X2, wherein the less than 5 additional amino acids flank the alpha 3 domain in a native HLA-G isoform.

6. The method of claim 1, wherein the multimer is a multimer of identical monomers.

7. The method of claim 1, wherein the multimer is a dimer.

8. The method of claim 1, wherein the two monomers each consist of SEQ ID NO: 3.

9. The method of claim 1, wherein the pharmaceutical composition comprises from 10 ng to 100 mg of the multimer.

10. The method of claim 1, wherein the pharmaceutical composition comprises a pharmaceutically acceptable vehicle or carrier.

11. The method of claim 1, wherein the method of treating graft rejection treats graft rejection of transplanted heart, skin, kidney, liver, or lung tissue in a subject in need thereof.

* * * * *

SEQUENCE LISTING

<160> NUMBER OF SEQ ID NOS: 8

<210> SEQ ID NO 1
<211> LENGTH: 92
<212> TYPE: PRT
<213> ORGANISM: human
<220> FEATURE:
<223> OTHER INFORMATION: HLA-G alpha3 peptide

<400> SEQUENCE: 1

Asp Pro Pro Lys Thr His Val Thr His His Pro Val Phe Asp Tyr Glu
1               5                   10                  15

Ala Thr Leu Arg Cys Trp Ala Leu Gly Phe Tyr Pro Ala Glu Ile Ile
            20                  25                  30

Leu Thr Trp Gln Arg Asp Gly Glu Asp Gln Thr Gln Asp Val Glu Leu
        35                  40                  45

Val Glu Thr Arg Pro Ala Gly Asp Gly Thr Phe Gln Lys Trp Ala Ala
50                  55                  60

Val Val Val Pro Ser Gly Glu Glu Gln Arg Tyr Thr Cys His Val Gln
65                  70                  75                  80

His Glu Gly Leu Pro Glu Pro Leu Met Leu Arg Trp
                85                  90

<210> SEQ ID NO 2
<211> LENGTH: 90
<212> TYPE: PRT
<213> ORGANISM: human
<220> FEATURE:
<223> OTHER INFORMATION: HLA-G alpha1 peptide

<400> SEQUENCE: 2

Gly Ser His Ser Met Arg Tyr Phe Ser Ala Ala Val Ser Arg Pro Gly
1               5                   10                  15

Arg Gly Glu Pro Arg Phe Ile Ala Met Gly Tyr Val Asp Asp Thr Gln
            20                  25                  30

Phe Val Arg Phe Asp Ser Asp Ser Ala Cys Pro Arg Met Glu Pro Arg
        35                  40                  45

Ala Pro Trp Val Glu Gln Glu Gly Pro Glu Tyr Trp Glu Glu Glu Thr
50                  55                  60

Arg Asn Thr Lys Ala His Ala Gln Thr Asp Arg Met Asn Leu Gln Thr
65                  70                  75                  80

Leu Arg Gly Tyr Tyr Asn Gln Ser Glu Ala
                85                  90

<210> SEQ ID NO 3
<211> LENGTH: 108
<212> TYPE: PRT
<213> ORGANISM: Artificial
<220> FEATURE:
<223> OTHER INFORMATION: Description of Artificial sequence: synthetic
      alpha3-L1 peptide

<400> SEQUENCE: 3

Gly Cys Gly Gly Gly Gly Ser Gly Gly Gly Ser Arg Ala Asp Pro
1               5                   10                  15

Pro Lys Thr His Val Thr His Pro Val Phe Asp Tyr Glu Ala Thr
            20                  25                  30

Leu Arg Cys Trp Ala Leu Gly Phe Tyr Pro Ala Glu Ile Ile Leu Thr
        35                  40                  45

Trp Gln Arg Asp Gly Glu Asp Gln Thr Gln Asp Val Glu Leu Val Glu

```
                 50                  55                  60
Thr Arg Pro Ala Gly Asp Gly Thr Phe Gln Lys Trp Ala Ala Val Val
 65                  70                  75                  80

Val Pro Ser Gly Glu Glu Gln Arg Tyr Thr Cys His Val Gln His Glu
                 85                  90                  95

Gly Leu Pro Glu Pro Leu Met Leu Arg Trp Lys Gln
                100                 105

<210> SEQ ID NO 4
<211> LENGTH: 184
<212> TYPE: PRT
<213> ORGANISM: human
<220> FEATURE:
<223> OTHER INFORMATION: HLA-G alpha1-alpha3 peptide

<400> SEQUENCE: 4

Gly Ser His Ser Met Arg Tyr Phe Ser Ala Ala Val Ser Arg Pro Gly
 1               5                  10                  15

Arg Gly Glu Pro Arg Phe Ile Ala Met Gly Tyr Val Asp Asp Thr Gln
                 20                  25                  30

Phe Val Arg Phe Asp Ser Asp Ser Ala Cys Pro Arg Met Glu Pro Arg
             35                  40                  45

Ala Pro Trp Val Glu Gln Glu Gly Pro Glu Tyr Trp Glu Glu Glu Thr
 50                  55                  60

Arg Asn Thr Lys Ala His Ala Gln Thr Asp Arg Met Asn Leu Gln Thr
 65                  70                  75                  80

Leu Arg Gly Tyr Tyr Asn Gln Ser Glu Ala Asp Pro Pro Lys Thr His
                 85                  90                  95

Val Thr His His Pro Val Phe Asp Tyr Glu Ala Thr Leu Arg Cys Trp
                100                 105                 110

Ala Leu Gly Phe Tyr Pro Ala Glu Ile Ile Leu Thr Trp Gln Arg Asp
            115                 120                 125

Gly Glu Asp Gln Thr Gln Asp Val Glu Leu Val Glu Thr Arg Pro Ala
        130                 135                 140

Gly Asp Gly Thr Phe Gln Lys Trp Ala Ala Val Val Val Pro Ser Gly
145                 150                 155                 160

Glu Glu Gln Arg Tyr Thr Cys His Val Gln His Glu Gly Leu Pro Glu
                165                 170                 175

Pro Leu Met Leu Arg Trp Lys Gln
            180

<210> SEQ ID NO 5
<211> LENGTH: 114
<212> TYPE: PRT
<213> ORGANISM: Artificial
<220> FEATURE:
<223> OTHER INFORMATION: Description of Artificial sequence: synthetic
      alpha3-L2 peptide

<400> SEQUENCE: 5

Cys Ala Ser Asp Ser Asp Phe Arg Val Phe Gln Thr Asp Lys Glu Met
 1               5                  10                  15

Leu Gln Arg Ala Asp Pro Pro Lys Thr His Val Thr His His Pro Val
                 20                  25                  30

Phe Asp Tyr Glu Ala Thr Leu Arg Cys Trp Ala Leu Gly Phe Tyr Pro
             35                  40                  45

Ala Glu Ile Ile Leu Thr Trp Gln Arg Asp Gly Glu Asp Gln Thr Gln
 50                  55                  60
```

```
Asp Val Glu Leu Val Glu Thr Arg Pro Ala Gly Asp Gly Thr Phe Gln
 65                  70                  75                  80

Lys Trp Ala Ala Val Val Pro Ser Gly Glu Glu Gln Arg Tyr Thr
                 85                  90                  95

Cys His Val Gln His Glu Gly Leu Pro Glu Pro Leu Met Leu Arg Trp
                100                 105                 110

Lys Gln

<210> SEQ ID NO 6
<211> LENGTH: 338
<212> TYPE: PRT
<213> ORGANISM: human
<220> FEATURE:
<223> OTHER INFORMATION: HLA-G

<400> SEQUENCE: 6

Met Val Val Met Ala Pro Arg Thr Leu Phe Leu Leu Leu Ser Gly Ala
 1               5                  10                  15

Leu Thr Leu Thr Glu Thr Trp Ala Gly Ser His Ser Met Arg Tyr Phe
                 20                  25                  30

Ser Ala Ala Val Ser Arg Pro Gly Arg Gly Glu Pro Arg Phe Ile Ala
             35                  40                  45

Met Gly Tyr Val Asp Asp Thr Gln Phe Val Arg Phe Asp Ser Asp Ser
 50                  55                  60

Ala Cys Pro Arg Met Glu Pro Arg Ala Pro Trp Val Glu Gln Glu Gly
 65                  70                  75                  80

Pro Glu Tyr Trp Glu Glu Glu Thr Arg Asn Thr Lys Ala His Ala Gln
                 85                  90                  95

Thr Asp Arg Met Asn Leu Gln Thr Leu Arg Gly Tyr Tyr Asn Gln Ser
                100                 105                 110

Glu Ala Ser Ser His Thr Leu Gln Trp Met Ile Gly Cys Asp Leu Gly
            115                 120                 125

Ser Asp Gly Arg Leu Leu Arg Gly Tyr Glu Gln Tyr Ala Tyr Asp Gly
130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Lys Gln Ser Ser Leu Pro
    290                 295                 300
```

```
-continued

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
                325                 330                 335

Ser Asp

<210> SEQ ID NO 7
<211> LENGTH: 12
<212> TYPE: PRT
<213> ORGANISM: Artificial
<220> FEATURE:
<223> OTHER INFORMATION: Description of Artificial sequence: synthetic
      linker L1

<400> SEQUENCE: 7

Gly Cys Gly Gly Gly Gly Ser Gly Gly Gly Gly Ser
1               5                   10

<210> SEQ ID NO 8
<211> LENGTH: 18
<212> TYPE: PRT
<213> ORGANISM: Artificial
<220> FEATURE:
<223> OTHER INFORMATION: Description of Artificial sequence: synthetic
      linker L2

<400> SEQUENCE: 8

Cys Ala Ser Asp Ser Asp Phe Arg Val Phe Gln Thr Asp Lys Glu Met
1               5                   10                  15

Leu Gln
```